(12) United States Patent
Pini et al.

(10) Patent No.: US 8,795,262 B2
(45) Date of Patent: Aug. 5, 2014

(54) OPTICAL FIBER LASER DEVICE AND METHOD FOR OCULAR SUTURING

(75) Inventors: Roberto Pini, Impruneta (IT); Luca Menabuoni, Impruneta (IT); Ivo Lenzetti, Prato (IT); Francesca Rossi, Sesto Fiorentino (IT); Jean-Marie Parel, Miami, FL (US)

(73) Assignees: Azienda USL 4 Prato, Prato (IT); Consiglio Nazionale Delle Ricerche, Rome (IT)

( * ) Notice: Subject to any disclaimer, the term of this patent is extended or adjusted under 35 U.S.C. 154(b) by 1865 days.

(21) Appl. No.: 11/991,343

(22) PCT Filed: Aug. 30, 2005

(86) PCT No.: PCT/IT2005/000501
§ 371 (c)(1),
(2), (4) Date: Feb. 29, 2008

(87) PCT Pub. No.: WO2007/026382
PCT Pub. Date: Mar. 8, 2007

(65) Prior Publication Data
US 2009/0312749 A1    Dec. 17, 2009

(51) Int. Cl.
| | |
|---|---|
| *A61F 9/008* | (2006.01) |
| *A61B 18/22* | (2006.01) |
| *A61F 13/00* | (2006.01) |
| *A61F 2/14* | (2006.01) |
| *A61F 2/16* | (2006.01) |
| *A61F 9/00* | (2006.01) |
| *A61F 2/30* | (2006.01) |

(52) U.S. Cl.
CPC ............. *A61F 9/0008* (2013.01); *A61F 9/0017* (2013.01); *A61F 2002/30062* (2013.01); *A61F 13/00* (2013.01)

USPC .................................... 606/4; 606/5; 623/4.1

(58) Field of Classification Search
USPC ............................................................ 606/4
See application file for complete search history.

(56) References Cited

U.S. PATENT DOCUMENTS

| | | | |
|---|---|---|---|
| 6,358,279 B1 | 3/2002 | Tahi et al. | 623/4.1 |
| 6,572,608 B1 | 6/2003 | Lee et al. | 606/15 |
| 8,092,490 B2* | 1/2012 | Redmond et al. | 606/214 |
| 2005/0010244 A1* | 1/2005 | Melles | 606/166 |

OTHER PUBLICATIONS

PCT Written Opinion mailed on Sep. 27, 2006 for PCT Application No. PCT/IT2005/000501 filed Aug. 30, 2005 in the name of Azienda USL 4 Prato.

(Continued)

*Primary Examiner* — Lakshmi Channavajjala
(74) *Attorney, Agent, or Firm* — Steinfl & Bruno LLP

(57) ABSTRACT

A method of suturing the lens capsule of the eye in the event of accidental rupture thereof or to create a valve and/or to close a capsulorhexis by laser-induced welding onto the capsule's surface of a flap of biocompatible biological tissue prepared so as to be optically absorbent at the wavelength of the laser being used for welding. The method is suitable for use in so-called Phaco-Ersatz or "lens refilling" ophthalmologic surgery. Welding is desirably performed using laser devices that comprise a laser generator and a fiberoptic system for conveying the laser beam, complete with an applicator handpiece suitable for use in welding the flaps onto the lens capsule in a liquid environment. The handpiece is shaped so as to exert moderate pressure on the tissues to be welded with the free end of the optic fiber.

8 Claims, 2 Drawing Sheets

(56) References Cited

OTHER PUBLICATIONS

PCT International Search Report mailed on Sep. 27, 2006 for PCT Application No. PCT/IT2005/000501 filed Aug. 30, 2005 in the name of Azienda USL 4 Prato.

PCT International Preliminary Report on Patentability mailed on Mar. 4, 2008 for PCT Application No. PCT/IT2005/000501 filed Aug. 30, 2005 in the name of Azienda USL 4 Prato.

McNally-Heintzelman, Laser Tissue Welding, Chap. 39 in Biomedical Photonics Handbook, 2003.

Rossi et al., Experimental study on the healing process following laser welding of the cornea, Journal of Biomedical Optics 2005, 10: 1-7.

Tang et al., Morphologic changes in collagen fibers after 830 nm diode laser welding, Lasers in Surgery and Medicine 1997, 21: 438-443.

Haefliger et al., Accommodation of an endocapsular silicone lens (Phaco-Ersatz) in the aging rhesus monkey, Journal of Refractive Corneal Surgery 1994, 10: 550-555.

Nishi et al., Accommodation amplitude after lens refilling with injectable silicone by sealing the capsule with a plug in primates, Archives of ophthalmology 1998, 116: 1358-1361.

Chan BP, A Photochemical Crosslinking Technology for Tissue Engineering—Enhancement of the Physico-Chemical Properties of Collagen-based Scaffolds, Proceedings of SPIE 2005, 5695: 317-327.

Landsman et al., Light-absorbing properties, stability, and spectral stabilization of indocynanine green, J. Appl. Physiol. 1976, 40: 575-583.

\* cited by examiner

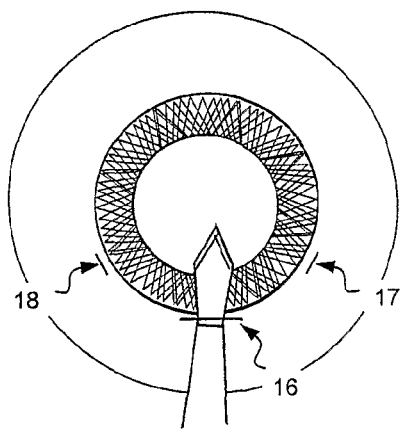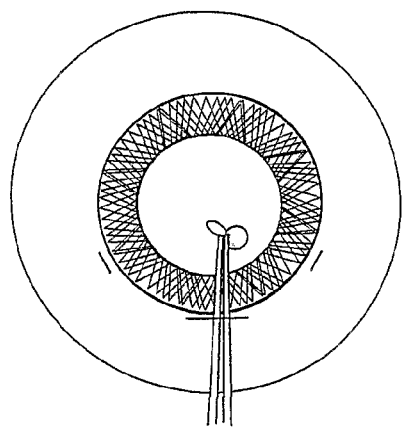
Fig. 4                               Fig. 5
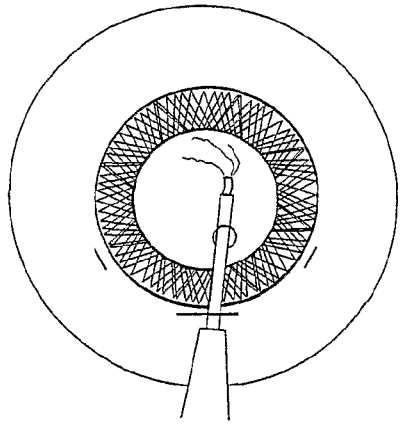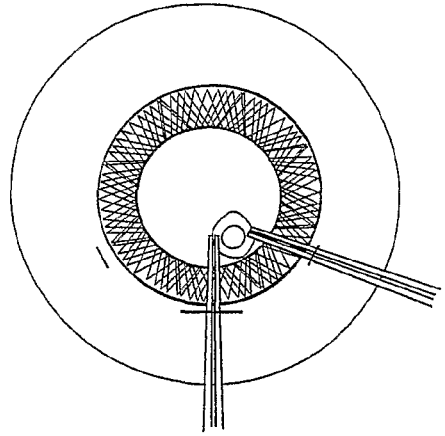
Fig. 6                               Fig. 7
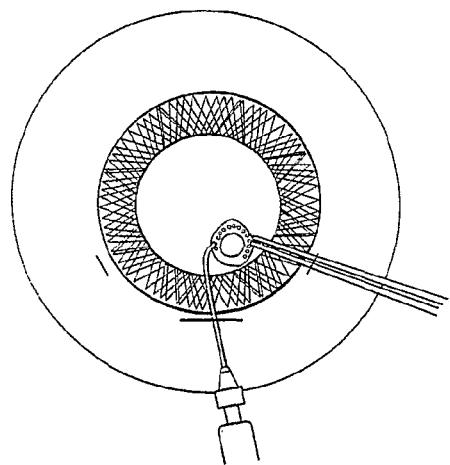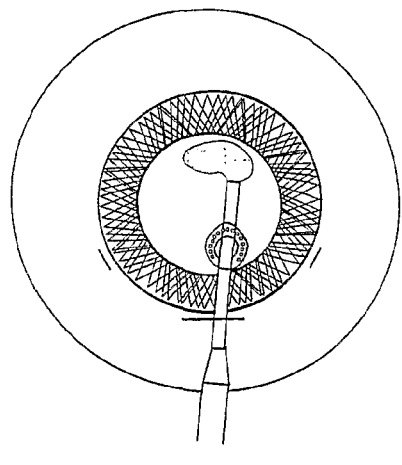
Fig. 8                               Fig. 9

OPTICAL FIBER LASER DEVICE AND METHOD FOR OCULAR SUTURING

FIELD OF THE INVENTION

The present invention relates generally to medical technology and, more particularly, to methods and devices for using biological tissues for surgical repair and the like.

BACKGROUND OF THE INVENTION

Conventional laser-induced welding techniques of biological tissues have been proposed and studied at an experimental level to assess their possible application in surgery with a view to suturing various types of tissue, e.g., skin, blood vessel walls, nerve tissue and others [K.M. McNally-Heintzelman, "*Laser Tissue Welding*", Chap. 39 in: Biomedical Photonics Handbook, pp. 39-1/39-45, T. Vo-Dinh, Ed., CRC Press, Boca Raton (2003)]. These techniques are based generally on the application of laser radiation to the biological tissues, which has the effect of activating certain proteins in the extracellular matrix, such as collagen and elastin, and inducing the immediate adhesion of the wound edges.

The recommended lasers used with this method are generally of the continuous emission type, with wavelengths coming in the visible and infrared spectral bands, e.g. argon, neodymium:YAG, diode and $CO_2$ lasers.

In some cases, the method involves using an exogenous chromophore (such as a biocompatible stain) with a high optical absorption at the wavelength of the laser being used. Said chromophore is applied locally to the edges of the surgical wound to suture and acts as a selective absorber of the laser radiation to enable a more controlled and localized welding effect, minimizing the risk of side-effects such as heat damage to the tissues adjacent to the treatment field.

In ophthalmic surgery, the laser-induced welding of biological tissues can be exploited for various purposes, as an alternative for instance to conventional suturing methods for closing corneal lesions in cataract and corneal transplant surgery [F. Rossi, R. Pini, L. Menabuoni, R. Mencucci, U. Menchini, S. Ambrosini, G. Vannelli, "*Experimental study on the healing process following laser welding of the cornea*", Journal of Biomedical Optics 10, pp. 1-7 (2005)].

Various radiation methods are currently used in the laser welding of biological tissues, with and without the aid of a chromophore:

1) direct irradiation, e.g. by means of an articulated arm, especially for laser wavelengths that cannot be transmitted by optical fibers (e.g. those produced by the CO2 laser);

2) operating microscope-guided irradiation, in which case the wound to be welded can be scanned with a beam-splitter used to couple the laser beam to the optical microscope [J. Tang, G. Godlewski, S. Rouy, G. Delacretaz, "*Morphologic changes in collagen fibers after 830 nm diode laser welding*", Lasers in Surgery and Medicine 21, pp. 438-443 (1997)];

3) irradiation via optical fibers, keeping the end of the optical fiber emitting the beam a suitable distance from the surface of the tissue (typically a few millimeters away) to avoid soiling the fiber, especially if a stain is used, since this would lead to a substantial reduction in the power transmitted.

One of the problems that remain to be solved in ophthalmgic surgery is how to repair the capsule containing the lens, because the wall of the capsule is extremely slender (10 micrometers) and under considerable tension, so conventional sutures cannot be used. For instance in cataract surgery involving the implantation of an intraocular lens (IOL), the rear wall of the capsule must be preserved in order to prevent the vitreous humor from penetrating into the anterior chamber. One of the most common complications of this type of surgery is represented by the perforation or laceration of the capsule wall as a result of an erroneous manipulation by the surgeon.

The problem of capsule repair is also still without solution in cases of perforating trauma involving the lens, which often gives rise to a severe inflammatory reaction (anaphylactic uveitis), followed by the onset of a post-traumatic cataract. These complications might be avoided if an efficient capsule suturing method were available.

A "Phaco-Ersatz" or "lens refilling" method has recently been proposed for use in ophthalmic surgery, whose purpose is the aspiration of the lens and subsequent refilling of the capsule with a biocompatible polymer that simulates the optical and mechanical properties of the young lens tissue, thereby restoring the transparency and accommodation function of the healthy lens [E. Haefliger, J-M. Parel, "*Accommodation of an endocapsular silicone lens (Phaco-Ersatz) in the aging rhesus monkey*", Journal of Refractive Corneal Surgery 10, pp. 550-555 (1994)]. It would have a lot of applications in the treatment of some of the most common ocular disorders, such as presbyopia and lens opacification (cataract). One of the problems still to be solved before the method can be used in clinical practice, however, is how to close the opening in the capsule (or rhexis) used to aspirate the old lens and subsequently refill the capsule.

Mechanical sealing devices have been proposed to solve this problem, such as plastic valves, but these have to be removed at a later date [O. Nishi, K. Nishi, "*Accommodation amplitude after lens refilling with injectable silicone by sealing the capsule with a plug in primates*", Archives of Ophthalmology 116, pp. 1358-61 (1998)]. Such mechanical valves have been tested at experimental level in an animal model to fill the capsule without the polymer leaking into the anterior chamber, but they would hardly be suitable for use in humans because, if they were left in place, they would become a foreign body that would partially obstruct the vision, interfering with lens accommodation and giving rise to various inflammatory or rejection processes during the healing period. Moreover, removing them—after the polymer has been irradiated from the outside to ensure its polymerization—would involve accessing the anterior chamber again and, in any case, the rhexis in the capsule would be left open.

OBJECTS AND SUMMARY OF THE INVENTION

Accordingly, it is an object of the present invention to provide a method of suturing, repairing and sealing ocular structures that would not involve any risk of post-operative rejection or inflammatory reactions, nor give rise to an obstruction to vision nor require the use of suturing materials, mechanical devices or adhesives that would remain as a foreign body on the surface of the ocular structure.

A specific object of the present invention is to provide a method of the above-mentioned type for use in repairing perforations and/or lacerations of the lens capsule tissue following an erroneous surgical maneuver or accidental trauma.

Another specific object of the present invention is to provide a method of the above-mentioned type suitable for use, in the so-called "Phaco-Ersatz" surgical technique, to create a valve on the capsulorhexis that enables the capsule to be filled without any leakage into the anterior chamber and the rhexis to then be permanently sealed without obstructing the patient's vision.

A further specific object of the present invention is to provide a method of the above-mentioned type wherein the lens capsule is sealed by applying flaps of biocompatible biological and optically transparent tissue and welding said flaps to the capsule by means of laser radiation.

It is still another specific object of the present invention to provide a method of the above-stated type wherein the flaps of biocompatible biological tissue are made capable of selectively absorbing the laser radiation by means of a treatment with a chromophore that serves the purpose of localizing the effect of the laser-induced welding and thus reducing the heat damage to tissues adjacent to the area to be treated.

A further object of the present invention is to provide a method for preparing flaps of biocompatible biological tissue suitable for use in suturing, repairing and sealing ocular structures by means of a laser-induced welding method, and particularly in the creation of a valve and/or closure on the lens capsule both in its normal physiological state and after it has been emptied of its contents.

Another object of the present invention is to provide a device for the laser-induced welding of flaps of biological tissue in a fluid environment.

Another object of the present invention is to provide a device of the above-mentioned type comprising a laser generator and a fiber-optic system for conveying the laser beam by means of an applicator handpiece suitable for welding the flaps of biocompatible biological tissue onto the lens capsule so that they serve both as a valve and as a final seal over a capsulorhexis.

These objects are achieved by the method for suturing, repairing and sealing ocular structures and the method for preparing biocompatible biological tissue flaps, and the device for laser welding in a fluid environment according to the present invention, the fundamental characteristics of which are set forth in claims 1, 8, 12 and 14, while further important characteristics of the invention are stated in the dependent claims.

BRIEF DESCRIPTION OF THE DRAWINGS

A specific, illustrative device and method for suturing, repairing and sealing ocular structures, and method of preparing biocompatible biological tissue flaps, according to the present invention, is described below with reference to the accompanying drawings, in which:

FIGS. 4, 5, 6, 7, 8 and 9 show schematically a surgical procedure involved in aspirating the lens and refilling the capsule with a biocompatible polymer (the Phaco-Ersatz method) through a valve made according to the invention.

The same numerals are used throughout the drawing figures to designate similar elements. Still other objects and advantages of the present invention will become apparent from the following description of the preferred embodiments.

DETAILED DESCRIPTION OF THE PREFERRED EMBODIMENTS

Figure 1:
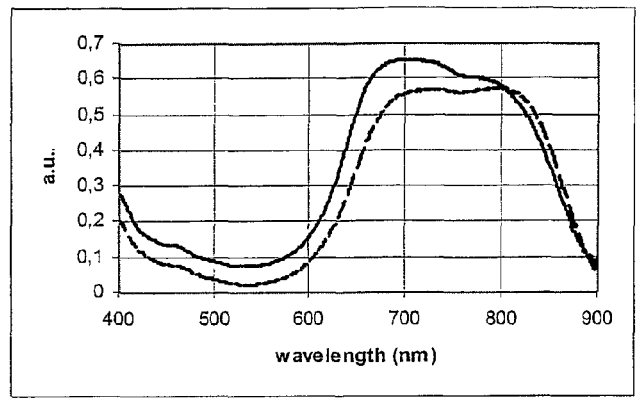
FIG. 1 shows a typical absorption spectrum for porcine capsular tissue stained with Indocyanine Green in a sterile water solution, as measured in fresh tissue (continuous line) and in tissue that has been dehydrated and then rehydrated 7 days later (dotted line)

Referring now to the drawings and, more particularly, to FIGS. 1-9, there is shown generally a specific, illustrative device and method for suturing, repairing and sealing ocular structures, according to various aspects of the present invention. In one embodiment, illustrated generally in FIG. 1, the method involves the use of flaps, of biocompatible biological tissue that are applied and welded over a discontinuity or perforation in an ocular structures using a laser-induced welding method. Having to operate in a liquid environment, such as the anterior chamber of the eye, the staining solution needed to ensure a selective absorption of the laser radiation cannot be applied topically to the two sides of tissue to be welded. Moreover, no liquid may come between the tissues to be welded during the welding process.

According to a preferred embodiment of the present invention, the flaps of tissue used for said purpose can be prepared from capsule tissue, particularly flaps of anterior capsule explanted post-mortem from a human donor (10 micron thick) or porcine tissue (30 micron thick). Said tissue consists essentially of collagen and elastin, with a limited cellular component, which is usually removed by washing at the time of its explantation. Alternatively, other natural biological tissues, such as amniotic membrane, or artificial tissues composed of collagen and/or elastin and suitably structured so as to reproduce the morphology, transparency and mechanical resistance of the above-mentioned natural tissues, may also be used (see for instance: B. P. Chan, "*A Photochemical Crosslinking Technology for Tissue Engineering—Enhancement of the Physico-Chemical Properties of Collagen-based Scaffolds*", Proceedings of SPIE Volume 5695, pp. 317-327 (2005)). For the sake of simplicity, in the following description reference will only be made to natural flaps of anterior capsule in the shape of a circular disc approximately 2 mm in diameter and a few tens micron thick. The method for preparing the flap is described in detail.

When the capsule is explanted from the donor, the flap of anterior capsule is spread on a microscope slide, with the original inner surface uppermost, since this is the one to stain with the chromophore. It is essential to control the flap's orientation throughout the preparatory stages in order to ensure that the donor flap is repositioned on the recipient capsule so that the curvatures of the two surfaces coincide, since this facilitates a better adhesion. Then the chromophore can be applied.

The choice of chromophore to use depends strictly on the type of laser that will be used because the absorption band of the chromophore has to include the emission wavelength of the laser to achieve the chromophore-mediated laser welding. In one possible embodiment, the chromophore consists of a sterile water solution of Indocyanine Green (indicated below by the abbreviation ICG), a substance widely used in ophthalic surgery, both as a contrast medium and as a photosensitizer, so its toxicological features are well known.

From the point of view of its optical properties, ICG has strong absorption features at near infrared wavelengths, around 800 nanometers. As known to a person skilled in the art, the shape of the absorption spectrum curve for ICG depends on the type of solvent used, the concentration of ICG in the solution (see for instance: M. L. J. Landsman, G. Kwant, G. A. Mook, W. G. Zijlstra, "*Light-absorbing properties, stability, and spectral stabilization of indocyanine green*", J. Appl. Physiol. 40, pp. 575-583 (1976)], and finally on the type of tissue to which the ICG binds. To obtain an efficient laser welding of the tissue stained with ICG, it is consequently fundamental to identify the optimal concentration of ICG in the solution to use beforehand, and subsequently have an apparatus available (preferably a portable unit suitable for use in the operating room) to check whether the flap stained with the solution has the right absorption coefficient for the wavelength of the laser generator.

In a possible embodiment of the present invention, the staining procedure is as follows: the flap is placed on the glass slide and kept adequately hydrated; using a calibrated microsyringe a drop of stain solution is applied to the exposed surface, taking care to avoid it spreading beyond the edges and thus staining the underside of the flap in contact with the glass. The drop is left in place for a few minutes (said time is optimized according to the type of tissue being used, typically 10 minutes for the example described herein) to allow for the stain to be absorbed by the exposed surface of the tissue. Then the flap is abundantly washed with sterile water to remove any residual traces of unabsorbed stain. The result is a flap stained only on the exposed side, which is the side that will be placed in contact with the surface of the recipient capsule when the laser-induced welding is performed.

Then measurements are taken to characterize the absorption spectrum of the stained flap. A laboratory spectrophotometer can be used to take the preliminary measurements for the preclinical optimization procedure, placing the stained flap in a normal analysis cell. As an example, the continuous line in FIG. 1 shows the typical absorption spectrum for a flap of porcine anterior capsule stained with one drop of a sterile water solution of ICG 4.4% left in place for 10 minutes before it was washed and measured with the spectrophotometer.

The spectrum clearly shows a wide absorption band between 700 and 800 nanometers, in which there can be comprised the emissions of various types of laser for the welding procedure, such as the aluminium gallium arsenide (AlGaAs) diode laser, which has an emission at approximately 800 nanometers, good efficiency characteristics and a more than adequate power rating for the needs of the present invention. In the description that follows, reference is made to this type of laser as the chosen source of radiation.

Figure 2:
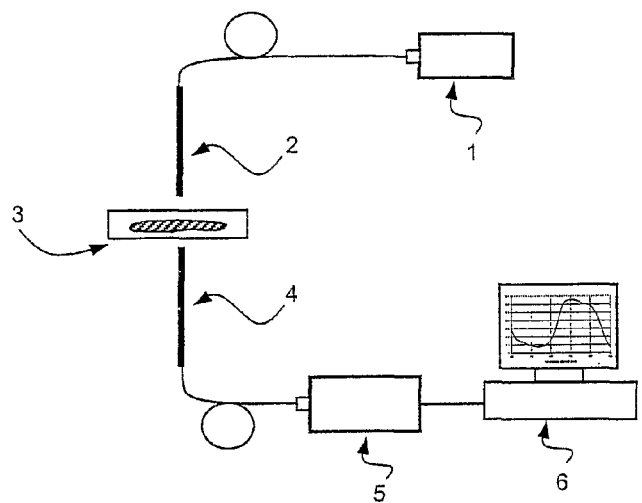
FIG. 2 is a block diagram representative of equipment for checking the absorption spectrum of the stained flap.

After identifying the ICG's optimal concentration and application times on the flap, the flaps to use in surgical practice in humans can be checked using an instrumentation of the type illustrated in FIG. 2, which has the advantage of being portable and not contaminating the flaps already sterilized for clinical use. With reference to the figure, the instrument comprises an illuminator 1, consisting of a tungsten-krypton lamp, for instance, with an optical fiber 2 for illuminating the capsule flap tissue contained in a sterile cell 3 made of transparent plastic material. The light that passes through the tissue is collected by a second optical fiber 4, connected to a portable spectrometer 5 (for instance, the illuminator lamp and spectrometer can be the Tungsten-Krypton SL1 light source and the Portable Spectrometer Mod. EPP-2000-VIS-100 manufactured by STELLAR NET Inc., USA). The spectrometer acquires the absorption spectrum of the stained flap, which is then saved on a computer 6.

After testing in this way, the flap can be used immediately for surgery, or it can be preserved, e.g. snap frozen in liquid nitrogen or dehydrated. With reference to FIG. 1, the dotted line shows the absorption spectrum of a flap of capsule that was dehydrated after staining and then rehydrated seven days later. It is possible to notice that the curve does not differ substantially from that of the fresh tissue, represented by the continuous line.

Figure 3:
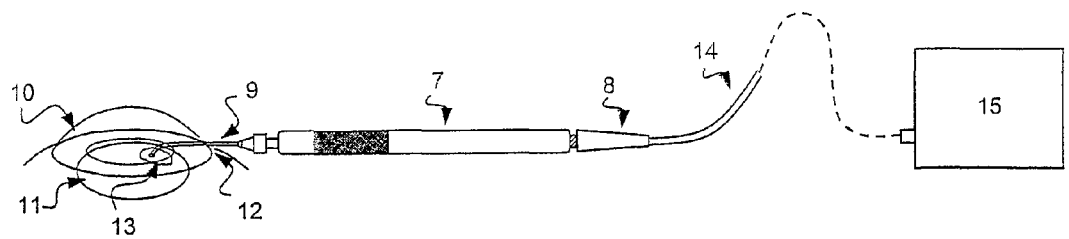
FIG. 3 shows one embodiment of a laser device, optic fiber and handpiece used to apply laser radiation, detailing how the handpiece is inserted in the anterior chamber of the eye.

The equipment forming the laser system for welding biological tissues, schematically illustrated in FIG. 3, comprises a laser 15 with a fiber-optic transmission 14 and an applicator handpiece 7. In a possible embodiment, said laser may be, as mentioned earlier, an AlGaAs diode laser emitting at 810 nm and a power of 0.5-10 W, capable of both continuous and pulsing operation, such as the Smarty A-800 laser manufactured by El.En. spa of Calenzano (FI), Italy. Said laser beam is transmitted via an optical fiber 14 with a 200 micron core connected to an applicator handpiece, according to the present invention.

FIG. 3 also shows a preferred embodiment of the applicator handpiece used to perform the laser welding of the flap in more detail. The handpiece includes a cylindrical grip 7 with the size of a pen, made of plastic or metal, with a spindle 8 at the rear end for locking the jacket of the optical fiber 14 in place, and a needle 9 at the front end, the terminal part of which is bent axially, with the end of the optical fiber extending therefrom. Said handpiece, like the optical fiber, is made of sterilizable materials suitable for clinical uses.

Referring again to FIG. 3, which shows a possible use of the handpiece forming the object of the present invention to close a capsulorhexis, the needle 9 is of a suitable length (e.g. 2-3 cm) for inserting in the anterior chamber of the eye, which is delimited between the cornea 10 and the lens 11, through a corneal or sclero-corneal tunnel, indicated by the numeral 12, in order to reach the surface of the lens capsule on which the flap of tissue 13 to be welded has been applied.

The bent shape of the needle 9 serves the purpose of enabling a moderate pressure to be exerted on the flap to be welded, thus ensuring a good contact between the flap and the surface of the capsule, expelling any fluid of the anterior chamber from the interface. In fact, this is an essential condition for an efficient laser welding between the surfaces of two biological tissues because, at microscopic level, a direct link has to be created between the collagen fibers on the two surfaces being welded together, thanks to the photo-thermal effect induced by the laser radiation.

On this aspect, staining only the side of the flap coming into contact with the surface of the recipient capsule serves to ensure that the laser radiation is only absorbed at the interface between said surfaces, so that the welding effect is highly localized and selective, with the advantage of enabling a reduction in the dose of laser radiation needed to complete the weld and thus also minimizing the risk of heat damage to the tissues adjacent to the treated area.

The absorption of the chromophore only on the surface interfacing with that of the capsular tissue, as described in the preparation of the materials, and the absence of any gap between the interfaces to be welded, ensured by the fact that the laser radiation is performed with the optical fiber in contact and exerting a moderate pressure that removes any liquid coming between the two surfaces, make it possible to obtain a laser welding of tissues even in a liquid environment such as that of the anterior chamber of the eye.

Moreover, the end of the optical fiber does not become soiled by said contact because the stained surface is the one on the other side of the flap, facing the surface of the capsule.

Thanks to said radiation by contact, the welding spot can be perfectly controlled both in terms of shape and size (the spot welds correspond exactly to the delivery area of the fiber, which is 200 micron in diameter) and in terms of the laser energy per unit of surface area (or fluency) applied to the tissue. In fact, this avoids any variability in the distance of the fiber from the irradiated surface, which affects the fluency because the emission of the fiber is inherently diverging. This makes the application of the laser welding highly reproducible.

The method for preparing the flaps and the equipment for the laser-induced welding of said flaps to ocular tissues according to the present invention consequently enables the creation of a valve and the sealing of a capsulorhexis, as needed, for instance, in the surgical procedure based on the Phaco-Ersatz technique.

FIGS. 4, 5, 6, 7 and 8 show the principal steps in said procedure, and schematically illustrate the anterior chamber of the eye as seen through the cornea. In particular, FIG. 4 shows the preparation of an access route into the anterior chamber using a method similar to the one adopted in cataract phaco-emulsification surgery, i.e. by means of a sclero-corneal tunnel 16 created surgically with a precalibrated scalpel (2.75-3.5 mm wide); one or two narrower (1 mm) additional service channels, indicated by the numerals 17 and 18 in FIG. 4, are usually also created to facilitate intraocular maneuvers. The next step, as illustrated in FIG. 5, is the capsulorhexis approximately 1 mm in diameter on the anterior capsule. Said rhexis is used to aspirate the contents of the lens, e.g. using a phaco-emulsifier as illustrated in FIG. 6, then the capsule can be refilled with hyaluronic acid, injected through the capsulorhexis.

The tissue flap prepared as explained earlier is then inserted through the sclero-corneal tunnel 16 and positioned on the anterior capsule, as schematically shown in FIG. 7, with the aid of microtweezers, so as to cover the rhexis entirely. Great care is taken during this step to ensure that the stained side faces the surface of the capsule. As shown in FIG. 8, the flap is welded around the circumference of the rhexis using the applicator handpiece and the radiation technique previously described, according to the present invention.

In the example in FIG. 8, the welding is completed by means of adjacent spot welds. Instead of completing the weld around the full circumference of the flap, one quadrant of the flap is initially left free. The partially welded flap thus serves as a valve through which the capsule can subsequently be filled with a biocompatible polymer, as shown in FIG. 9. Finally, the valve is closed using the method already illustrated in FIG. 8, completing the welding around the full circumference so as to seal in the contents. Where necessary, the polymer used to fill the capsule can be submitted to irradiation from the outside to induce its polymerization without any need to remove the capsule at the end of said operation.

It should be noted that the welding can only be done efficiently for certain laser emission parameters, which depend on the type of tissue being irradiated and the concentration of stain. Referring to the preferred embodiment described herein, as a non-limiting example, a pulsing radiation method can be used for the laser-induced welding of capsule tissue, instead of the continuous irradiation more frequently used for other types of tissue. Said pulsing mode is particularly suitable for the contact-type welding procedure forming the object of the present invention and has the advantage of reducing the interaction time with the ocular structures, which are particularly vulnerable, thereby limiting the propagation of heat to the adjacent tissues and the related risk of heat damage. Typical parameters for use with this irradiation method are, for instance: a pulse duration between 50 and 150 ms, with a single-pulse energy coming between 20 and 100 milliJoules.

Finally, it should be noted that the method according to the present invention can also be advantageously applied to fix corneal or intraocular prostheses, e.g. contact lenses, IOL, and so on, as well as to contain retinal detachments or seal retinal perforations.

Various modifications and alterations may be appreci-ated based on a review of this disclosure. These changes and additions are intended to be within the spirit and scope of the present invention, as defined by in the following claims.

What is claimed is:

1. A method of suturing, repairing and sealing ocular structures, which comprises
   using a flap of optically transparent, biocompatible biological tissue for application over a surface discontinuity or perforation in the ocular structure,
   positioning, over the discontinuity or perforation, the flap with a biocompatible chromophore, so that a side of the flap treated with the chromophore is facing and in contact with a surface of the ocular structure, the biocompatible chromophore being located limitedly to said side of a flap, and
   subsequently fixing the flap to the surface of the ocular structure by photothermal laser-induced welding, wherein the photothermal laser-induced welding is obtained by irradiation of a laser beam emitted from an end of an optic fiber connected to a laser generator, the end being brought into contact with the flap and exerting pressure thereon in order to seal the discontinuity or perforation, the biocompatible chromophore having an optical absorbance band including an emission wavelength of the laser beam.

2. The method set forth in claim 1, wherein the ocular structure is the lens capsule and the surface discontinuity or perforation is incurred as a result of an erroneous surgical maneuver or following accidental trauma.

3. A method as set forth in claim 1, wherein the ocular structure is the lens capsule and the surface discontinuity or perforation is a capsulorhexis performed as part of the Phaco-Ersatz surgical technique, the flap being partially welded to the surface of the capsule surrounding the rhexis and thus serving as a valve for delivering a biocompatible material inside the capsule and subsequently, after welding has been completed, as a cover over the rhexis, for sealing in the contents of the capsule.

4. The method as set forth in claim 3, further comprising the steps of:
   a) preparing an access route into the anterior chamber of the eye by surgically creating a sclero-corneal tunnel to enable capsulorhexis and removal of the content of the capsule,
   b) inserting through the tunnel in the anterior chamber a flap of biocompatible biological tissue treated with a biocompatible chromophore chosen in such a way that its optical absorbance band includes the emission wave length of the laser being used,
   c) applying the flap over the anterior capsule at the rhexis so that the side of the flap treated with the chromophore is facing and in contact with the surface of the capsule,
   d) partially welding the flap onto the surface of the capsule by irradiation with the laser beam transmitted through the optic fiber, in such a way to leave a passage for the delivery of a biocompatible material, and
   e) completing the welding around the flap on the surface of the capsule to seal the rhexis formed thereon.

5. The method set forth in claim 1, wherein the flap undergoes a test on its absorbance before it is attached to a lens capsule.

6. The method set forth in claim 1, wherein the flap of biocompatible biological tissue is of natural or artificial type.

7. The method set forth in claim 6, wherein the flap of natural type, biocompatible biological tissue is lens capsule tissue obtained from a human donor post-mortem, or from a pig, or an amniotic membrane.

8. The method of claim 1, wherein the chromophore is indocyanine green.

* * * * *